United States Patent [19]

Haight et al.

[11] Patent Number: 5,796,101

[45] Date of Patent: Aug. 18, 1998

[54] METHOD OF PROCESSING NUCLEIC ACIDS

[75] Inventors: Richard Allan Haight, Mahopac, N.Y.; Paul Fredrich Seidler, Ridgefield, Conn.

[73] Assignee: IBM Corporation, Armonk, N.Y.

[21] Appl. No.: 619,048

[22] Filed: Mar. 20, 1996

Related U.S. Application Data

[60] Provisional application No. 60/006,443, Nov. 13, 1995.
[51] Int. Cl.[6] ............................................. H01J 37/26
[52] U.S. Cl. ............................ 250/306; 250/307; 250/305
[58] Field of Search .............................. 250/306, 307, 250/305

[56] References Cited

U.S. PATENT DOCUMENTS 5,569,916 10/1996 Tomie ................................. 250/305

*Primary Examiner*—Kiet T. Nguyen
*Attorney, Agent, or Firm*—Barnes, Kisselle, Raisch, Choate, Whittemore & Hulbert, P.C.

[57] ABSTRACT

A laser based tunable high resolution ESCA (Electron Spectroscopy for Chemical Analysis) system in which harmonics of a subpicosecond laser source are used to carry out core level photoemission is provided wherein photon energies tunable to 80 eV have been achieved and energies up to 150 eV or more are possible. The harmonic light is of extremely narrow bandwidth and spectrally bright which can be focussed by using reflective optics of gratings to an extremely small spot of well below one micron to permit high spatial resolution. When used in conjunction with appropriate electron objects, high resolution chemically sensitive mapping of device-size features is possible.

21 Claims, 1 Drawing Sheet

5,796,101

1

METHOD OF PROCESSING NUCLEIC ACIDS

CROSS-REFERENCE TO RELATED APPLICATIONS

The present application claims priority to co-pending U.S. Provisional application 60/006,443 filed Nov. 13, 1995.

FIELD OF THE INVENTION

The present invention generally relates to a method and apparatus for a high resolution ESCA system using laser harmonics and more particularly, relates to a method and apparatus for a high resolution ESCA system using laser harmonics that have tunability, high count rate, high spatial resolution, and high energy resolution.

BACKGROUND OF THE INVENTION

At the present time, no laboratory-scale source of radiation is available for carrying out ESCA (Electron Spectroscopy for Chemical Analysis) that has the desirable characteristics of coherence, tunability, high spatial resolution, high time resolution, and narrow bandwidth. Sources that do exist are incoherent, line radiation sources such as MgKα, AlKα and rare gas resonance lamps, and they are not tunable. ESCA is a technique for identifying chemical species and oxidation states of the species present on or near the surface of a material. The technique involves focusing an ionizing radiation onto a material which liberates electrons which are then detected and analyzed to determine their kinetic energies. The ionizing radiation can be a line radiation from sources such as Mg, Al, synchrotron sources, or other X-ray sources.

It is generally known that two types of electrons are emitted when a material is bombarded with an ionizing radiation. The first kind of electrons are low binding energy, or valence electrons. These electrons are the ones which are involved in bonding. Their energy spectrum is broad or spread out in energy. The second type of electrons are the atomic core electrons. These electrons are not involved in bonding and their energy spectrum is sharp and therefore produce sharp lines in a photoemission spectrum. Their binding energies are specific to the atom from which they are emitted. The specific energy permits identification of the species present in or on the sample. For instance, the binding energy of the Si 2p core level is −99 eV. The binding energy of the Ge 3d core level is −29 eV and this difference allows one to discriminate Si from Ge.

Another added aspect in ESCA involves the oxidation state of the atom. For example, if Si is oxidized to form silicon dioxide, the Si 2p core level will move in energy to −104 eV because as Si donates electrons to the electronegative oxygen atoms the charge around the Si changes. This change in valence charge causes the Si core level to shift rigidly in energy (i.e., the level shifts but retains a sharp peak) in a well understood manner. These effects allow one to determine the species of atoms on or near a surface and the chemical state of the atom as well. The behavior has resulted in ESCA becoming an extremely important and useful analytical tool in the investigation of surface chemistry. By means of ESCA, complete sets of photoelectron lines can be observed from the core levels as well as from the valence levels.

Frequency tunability is critical for the study of cross-sectional and electron escape depth properties. As a result, a complete study cannot be carried out in a laboratory but must be accomplished at a large synchrotron radiation facility which is frequently difficult to access. In addition, known laboratory energy sources are not easily focussed to very small spot sizes necessary for the achievement of a desirable spatial resolution which is important in the examination of microscopic features in devices. Furthermore, for time-dependent studies, a pulsed energy source is needed. There are no available laboratory sources and at present the temporal pulse duration is inadequate at synchrotron facilities. While rare gas resonance lamp sources have very high energy resolution, they are restricted to only a few energetic lines. The more versatile, high-energy Mg and Al sources exhibit large energy bandwidths, i.e., >1 eV, which can only be reduced by monochromatizing the light with a significant concomitant loss of flux. Narrow bandwidth is important for discerning small chemical shift differences of atoms. The existing laboratory-scale energy sources therefore experimentally limit the ability to study many microscopic features and devices.

It is therefore an object of the present invention to provide a method and apparatus for a tunable high resolution ESCA system by using laser harmonics that does not have the drawbacks and shortcomings of the prior art ESCA systems.

It is another object of the present invention to provide a method and apparatus for a high resolution ESCA system by using laser harmonics that is capable of providing a tunable frequency.

It is a further object of the present invention to provide a method and apparatus for a tunable high resolution ESCA system by using laser harmonics that can be focussed to a very small spot size for achieving spatial resolution necessary for the examination of microscopic features.

It is another further object of the present invention to provide a method and apparatus for a tunable high resolution ESCA system by using laser harmonics that can be used to study the cross-section and the electron escape depth properties of materials.

It is still another object of the present invention to provide a method and apparatus for a tunable high resolution ESCA system by using laser harmonics that can be focussed down to a submicron size spot.

It is yet another object of the present invention to provide a method and apparatus for a tunable high resolution ESCA system by using laser harmonics up to the 39th harmonic, and beyond.

It is still another further object of the present invention to provide a method and apparatus for generating laser light which can be focussed to intensities of greater than $10^{14}$ W/cm$^2$ in a rare gas in order to produce broadly tunable harmonic light.

It is yet another further object of the present invention to provide a method and apparatus for a high resolution ESCA system by using tunable laser harmonics that are capable of high count rate, high spatial resolution, and high energy resolution.

SUMMARY OF THE INVENTION

In accordance with the present invention, a method and apparatus for a tunable high resolution ESCA system by using laser harmonics that are capable of submicron spatial resolution is provided.

In the preferred embodiment, a laser based tunable high resolution ESCA system, in which harmonics of a subpicosecond laser source are used to carry out core level photoemission, is provided. Photon energies tunable to 80 eV have been achieved and energies to 150 eV and beyond are possible. A tunable range for the present invention is between 6 and 80 eV. The harmonic light is of extremely narrow bandwidth and spectrally bright. Using reflective optics or reflective gratings to produce a single-frequency coherent harmonic, the light can be focussed to an extremely small spot of well below 1 micron that permits high spatial resolution of below 1 micron. Spatial resolution as low as 0.1 micron has been demonstrated. When used in conjunction with appropriate electron optics, high resolution chemically sensitive mapping of microelectronic device size features is possible. The intensity of the laser beam required in order to produce the harmonics is at least $10^{14}$ W cm$^{-2}$ which currently is supplied by a pulsed laser having a pulse width of less than 1 picosecond.

The present invention is further directed to a method of using a tunable high resolution ESCA system utilizing laser harmonics to study microscopic features and devices that require very high spatial resolution. The method can be carried out by first using an amplified dye laser to produce odd multiple harmonics in a noble gas for use in photoemission, a particular harmonic of interest is then selected with a reflective grating in the beam line. The frequency tuning is achieved by harmonic selection and controlled by rotating the grating. A secondary tuning is also possible by changing the input laser frequency. The grating also serves the purpose of focussing a beam onto a sample to be investigated which is frequently positioned in an ultrahigh vacuum chamber at the end of the X-ray beam line. The photoelectrons emitted at the focus point are then collected and studied by a kinetic-energy-resolving detector such as a time-of-flight or electrostatic analyzer.

BRIEF DESCRIPTION OF THE DRAWINGS

Other objects, features and advantages of the present invention will become apparent upon consideration of the specification and the appendant drawings, in which.

DETAILED DESCRIPTION OF THE PREFERRED EMBODIMENT

A method and apparatus for a tunable high resolution ESCA system using laser harmonics that are capable of submicron spatial resolution is disclosed.

Figure 1:
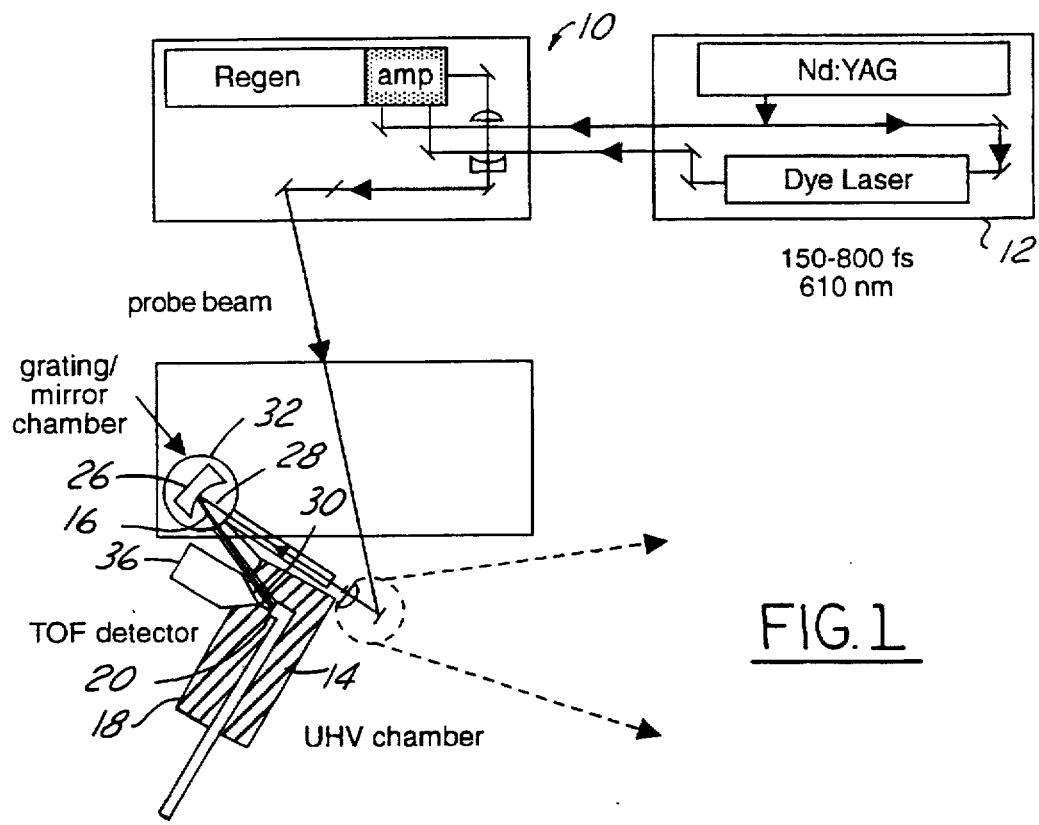
FIG. 1 is a schematic layout of the present invention apparatus.

An integrated system 10 that is suitable for laboratory use is shown in FIG. 1. System 10, which has the advantages of tunability, narrow bandwidth, high spatial resolution, and high focussability of the harmonic light, is used to produce the light for carrying out photoemission. Light pulses from a high intensity, high repetition rate, laser 12 emitting light having frequencies in the visible or near infrared ranges are focussed into a noble gas (e.g., Xe, Kr, Ar, Ne, He) at focus point 14 at the front of a beam line 16 attached to a sample analysis chamber 18. Beam line 16 may be differentially pumped along its length. A typical laser source that can be used includes a subpicosecond amplified dye laser or a titanium-sapphire laser (not shown). The amplification can be accomplished with a regenerative amplifier (regen-amp) as shown in FIG. 1. The intensity of the laser beam at the focus point 14 is preferably in excess of $10^{14}$ W cm$^{-2}$. The interaction of the laser light beam 15 with the noble gas at 14 produces odd multiple harmonics of the laser frequency, i.e., from the 3rd to the 39th harmonic (79 eV). Photon energies up to at least 150 eV can be produced with more powerful lasers. The resulting harmonic soft X-rays are then used for photoemission. In order to permit the transmission of the harmonics, the harmonics should be produced in a windowless environment, of chamber 32 and beam lines 16 with low gas pressure. A synchronized pulsed valve (not shown) is ideal for producing the desired local gas pressure of greater than about 1 torr (optimally 100 torr) at the input laser focus point 14. As is known, such valves generally comprise a piezoelectrically driven gas nozzle. In such valves, an electrical pulse synchronized with the laser is used to trigger a power supply which causes the nozzle to open. Behind the nozzle is a source of high pressure gas. Upon opening, a high pressure burst of gas occurs at the nozzle of the valve. The laser light is focussed at this point and the interaction of the high intensity laser field with the rare gas produces a series of odd multiple harmonics. These harmonics are photons with frequencies (energies) found at odd multiples of the input laser.

Once the laser harmonics are produced, a particular harmonic of interest is selected by using a reflective grating 26 in the beam line 16. For energies below 40 eV, a platinum coated normal incidence spherical grating can be used. At higher energies, a multiple layer-coated normal incidence grating may be employed. Alternatively, grazing incidence optics such as ellipsoidal or toroidal gratings (not shown) can be used. The reflective optics are advantageous since they exhibit no chromatic aberration. Slits such as those used in the synchrotron monochromators are not required in the present invention apparatus 10 since the bandwidth of the harmonic is determined by the pulse lengths of the input laser 12 and the harmonic conversion process. The harmonics are extremely narrow in bandwidth which allows for ultrahigh energy resolution of the photoemitted electrons. The bandwidth achievable can be a factor of 1,000 times better than those available with non-monochromatized X-ray line sources.

The frequency tuning of the present invention apparatus 10 is primarily achieved by the harmonic selection and is controlled by rotating the grating 26. Secondary tuning is possible by changing the input laser frequency of the dye laser 12. The frequency tuning in the present invention process is very important since the kinetic energy of the photoemitted electron is governed by the photon energy. The energy of the electron determines its escape depth. By controlling the escape depth, suitable surface or bulk sensitivity can be chosen. This allows the investigator a means to determine if the core level shifts observed have occurred at the surface or in the bulk of the material.

The grating 26 serves the purpose, other than selecting the harmonic, of focussing the beam onto sample 20 that is under investigation. The sample 20 may be a solid substrate or gas. It is usually positioned in the analysis chamber 18 of ultrahigh vacuum at the end of the X-ray beam line 16. Positioning means 17 are used to position sample 20 and to select various areas of sample 20 for examination. Since suitable means for performing this function are available, no further explanation is provided here. A suitable vacuum in chamber 18 is in the range between $10^{-5}$ and $10^{-11}$ torr. Photoelectrons emitted at the focus point on sample 20 are collected and observed by a kinetic-energy-resolving detector such as a time-of-flight detector 36 or an electrostatic analyzer (not shown).

Since the harmonic light used in the present invention method is pulsed at a repetition rate of 540 Hz, with pulsewidths below 1 picosecond, time-of-flight (TOF) analysis is an efficient method to measure the photoemitted electrons. TOF analysis permits the measurement of all possible electron energies on each laser shot, increasing the detector efficiency over standard single energy analyzers. The analyzer consists of a field free drift region, an electron multiplier, a multianode array, and associated pulse discrimination and timing electronics. A pair of microchannel plate electron multipliers are mounted in a ceramic holder positioned in front of 64 individual anodes distributed over the 40 mm diameter active area of the microchannel plates. The 64 gold anodes, deposited onto a specially fabricated glass to metal feed-through are arranged symmetrically in two sets of 32 parallel lines of varying length. Each anode represents a single electron detector so that for each laser shot up to 64 electrons can be processed.

The TOF can operate in two modes. The first involves a simple direct path between the sample and the detector. The advantages are the simplicity and the angular resolution. A second mode involves the use of a parabolic mirror which works in analogy to an optical parabolic mirror. If the sample is located at the focus of the mirror then the electrons emitted from a small spot on the sample are reflected by the mirror and focussed at infinity. This focus results in all electron trajectories being parallel and equal. The parallel trajectories allow the drift path to be as long as desired giving rise to much higher energy resolution. The multichannel plate and anode array can then be located at a distance of 1 meter or more from the sample resulting in high energy resolution. The large collection angle of the mirror increases the sensitivity over the simple TOF by a factor of 50. For ESCA this is desirable since core level electrons are emitted at all angles.

In addition to the desirable tunability and the narrow bandwidth of the present invention apparatus, several other advantages can also be achieved. For instance, the apparatus is a laboratory-scale system. It utilizes table-top lasers and analysis chambers that will fit into a standard-sized laboratory. Furthermore, because of its good spatial qualities, the harmonic light used for the photoemission is highly focussable. This is a very important property that is useful in spatial profiling for the characterization of a surface profile on a microscopic scale. Since the soft X-ray harmonic light is created in a non-linear process from a coherent laser source, the radiation is by its nature highly directional and coherent. Consequently, the soft X-rays can be focussed to near the diffraction limit. For the harmonic photons, spot sizes well below 1 micron are possible. Substantially smaller spot sizes are also achievable at higher energies. At such a small spot size, tunable ESCA can be carried out on microscopic or device-sized features. No special electron optics which would reduce electron flux to the detector, are needed to reduce the field of view. In other words, there is no trade-off of sensitivity for area selectivity. Contrast is achieved by the energetic chemical shifts of atomic core levels in different chemical environments.

A primary advantage of the present invention apparatus is the focussability which when combined with the avoidance of flux limiting components, such as monochromator slits, provides for high peak brightness of the X-ray source. The high repetition rate of the input laser produces a high duty cycle for data collection. The high brightness and the high duty cycle together ensure that spectra with good statistics such as high signal-to-background ratios of about 10 to 20 to 1 can be collected in a suitable length of time, e.g., about five minutes.

A further advantage of the present invention system is that because the X-rays for photoemission originate from a laser source that is polarized, the X-rays are also polarized. Anisotropic photoemission measurements are therefore possible by using the present invention apparatus which is not achievable with conventional ESCA systems.

The generation of X-rays for photoemission requires high peak laser intensities. The source is necessarily a pulsed source which in turn permits time-resolved experiments to be carried out. Intensities above $10^{14}$ W cm$^{-2}$ are best produced with subpicosecond lasers. As a result, subpicosecond time-resolution is achieved. This compares favorably with a time resolution of approximately 10 minutes possible from sequential scans with a conventional ESCA system.

The present invention apparatus therefore enables a laboratory-scale device for carrying out ESCA with a source of coherent, tunable, highly-focussable, narrow-bandwidth, pulsed, soft X-ray radiation. The radiation source derives from a high intensity, high repetition rate, visible or near infrared laser. The beam can be focussed to a greater than $10^{14}$ W cm$^{-2}$ intensity into a volume of noble gas to generate harmonics of the input laser frequency. The pressure of the noble gas is preferably produced by a synchronized pulsed valve.

The apparatus further includes a soft X-ray beam line in which the laser harmonic of interest is separated and focussed with a grating, an analysis chamber which contains the sample to be investigated, and onto which soft X-rays are focussed by the grating in the beam line. The apparatus also includes a detector for the electrons photoemitted from the sample capable of measuring the kinetic energy of these electrons. The detector is preferably a high-resolution time-of-flight detector or an electrostatic analyzer.

EXAMPLE

A present invention apparatus, as shown in FIG. 1, includes a table-top, amplified, subpicosecond dye laser system 12 operating at 540 Hz which provides intense pulses of visible light at 2 eV/photon for harmonic conversion. The light is focussed at the front of a simple beam line 16 into a pulsed jet of argon gas at 14 to generate the harmonics. Argon is an inexpensive, widely available gas which is easily pumped by turbo molecular pumps. Both platinum and multi-layer coated normal incidence spherical gratings 26 have been used to separate the harmonics. For more sensitive studies, thin aluminum foils (not shown) can be introduced into the X-ray beam line 16 to completely separate the sample under investigation from the residual argon gas. Photons with energies up to 80 eV (39th harmonic) have been generated in this manner. An ultra high vacuum system 18 houses the sample under investigation. A time-of-flight, multi-channel electron detector 36 is also coupled to the analysis chamber 18.

Figure 2:
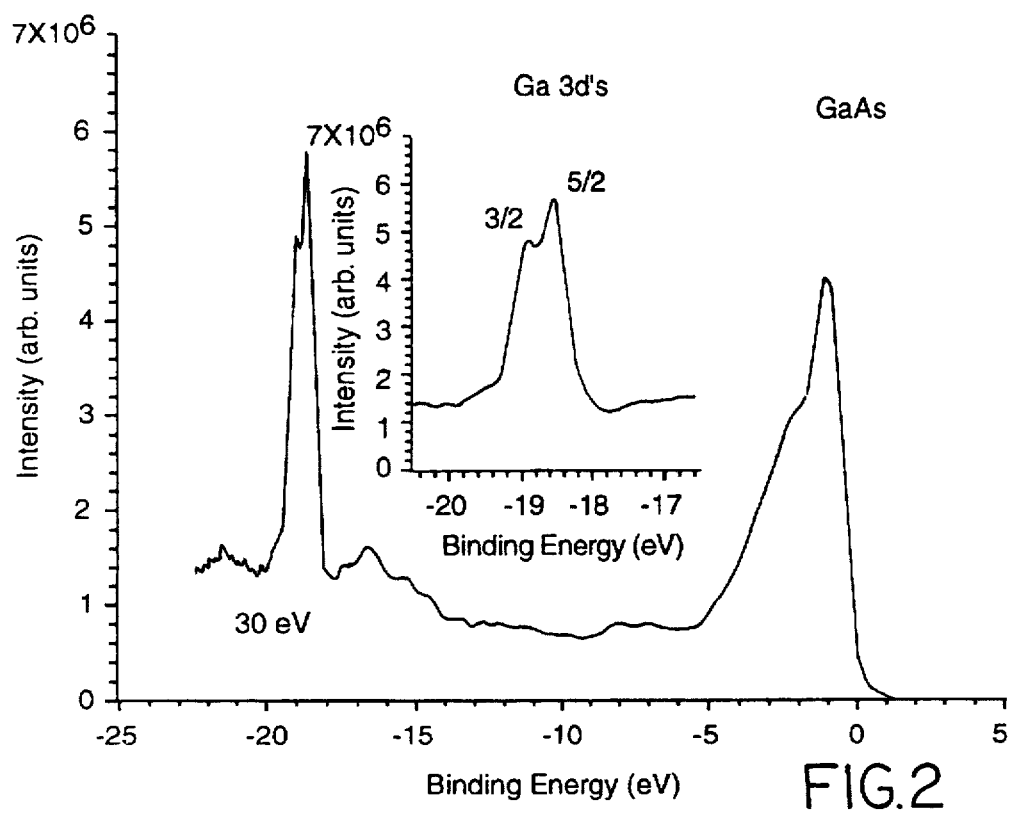
FIG. 2 is a sample ESCA graph for GaAs obtained by the present invention method.

In the example, high resolution core level spectra from a number of systems were investigated, including GaAs (where Ga 3d core levels show spin-orbit split components), Pb on Si (Pb 5d's), Bi on Si (Bi 5d's), Ge on Si (Ge 3d's) and In in the compound $In_2I_6$ (In 4d's). In FIG. 2, the Ga 3d levels indicated by the peak at −18.5 eV which are collected with 30 eV photons are shown. The spectrum required only 5 minutes to collect due to the high count rate achieved. The count rate is the rate of collection of electrons which indicates how fast spectra can be formed. The higher the count rate, the shorter time it takes to collect a spectrum. If the light source is weak, then it takes longer time to collect a spectrum.

The present invention method and apparatus can be adopted for research and investigations in core-level photoemission spectroscopy. It can be used by laboratories that do not have access to a synchrotron light source. The present invention method and apparatus can be especially suitable for use in the investigation of semiconductor devices (e.g., integrated circuit chip). For instance, the high energy and spatial resolution of the apparatus can be used to distinguish portions of a circuit composed of silicon nitride from those composed of silicon dioxide, since the core level binding energies for these chemically distinct components differ by several electron volts.

It should be noted that since soft X-ray photons are used in the present invention method instead of an electron beam as that used in Auger probes, electron-sensitive materials can be investigated by the present invention method without causing damage to the substrate. This makes the present invention method especially suitable for the investigation of microelectronic devices.

While the present invention has been described in an illustrative manner, it should be understood that the terminology used is intended to be in a nature of words of description rather than of limitation.

Furthermore, while the present invention has been described in terms of a preferred embodiment thereof, it is to be appreciated that those skilled in the art will readily apply these teachings to other possible variations of the invention. For instance, the present invention can be readily used to study different electronic materials deposited on a semiconductor chip. The tunable, high count rate, high spatial resolution laser harmonics can also be used for other spectroscopy as well while achieving the same desirable result.

The embodiments of the invention in which an exclusive property or privilege is claimed are defined as follows:

Having thus described our invention what we claim as new and desire to secure as Letters Patent, is:

1. A method of using a tunable, high resolution electron spectroscopy for chemical analysis (ESCA) system utilizing laser harmonics for investigating features on a sample with high spatial resolution comprising the steps of:
   providing a pulsed laser beam for producing odd multiple harmonics in a noble gas,
   selecting a predetermined laser harmonic by a reflective grating positioned in the path of said pulsed laser beam,
   focussing said predetermined laser harmonic into a small spot of less than 1 micron in diameter on a surface of said sample, and
   analyzing photoelectrons emitted by said sample surface at said focussed small spot.

2. A method according to claim 1, wherein said pulsed laser beam is supplied by a dye laser or a titanium-sapphire laser.

3. A method according to claim 2, wherein said dye laser or titanium-sapphire laser light is amplified by a regenerative amplifier.

4. A method according to claim 1, wherein said pulsed laser beam has a frequency in the visible or near infrared range.

5. A method according to claim 1, wherein said odd multiple harmonics are in the range of between the 3rd and the 39th harmonic.

6. A method according to claim 1, wherein said tunable range for said ESCA system includes photon energies in the range between about 6 and 150 eV.

7. A method according to claim 1, wherein said tunable range for said ESCA system includes more preferably photon energies of up to 80 eV.

8. A method according to claim 1, wherein the pressure of said noble gas is preferably produced by a synchronized pulsed valve.

9. A method according to claim 1, wherein said noble gas is selected from the group consisting of Xe, Kr, Ar, Ne, and He.

10. A method according to claim 8, wherein said noble gas has a minimum pressure of 1 torr.

11. A method according to claim 1, wherein said laser beam is focussed into the noble gas with a minimum intensity of $10^{14}$ W/cm$^2$.

12. A method according to claim 1, wherein said predetermined laser harmonic is focussed into a spot sufficiently small to study a microscopic feature on an integrated circuit chip.

13. A method according to claim 1, wherein said photoelectrons emitted by said sample surface are analyzed by a kinetic-energy-resolving detector.

14. A method according to claim 13, wherein said kinetic-energy-resolving detector is a time-of-flight electron detector or an electrostatic analyzer.

15. A method of using a tunable, high resolution electron spectroscopy for chemical analysis (ESCA) system which utilizes a laser harmonic selected from the 3rd to the 39th harmonic for the investigation of microscopic features on a sample comprising the steps of:
   providing a pulsed laser beam from a dye laser for producing odd multiple harmonics between the 3rd and the 39th harmonic in a noble gas selected from the group consisting of Xe, Kr, Ar, Ne, and He,
   selecting a predetermined laser harmonic by a reflective grating positioned in said pulsed laser beam, said harmonic having a photon energy in the range between about 6 and 150 eV,
   focussing said predetermined laser harmonic into a spot of less than 1 micron in diameter on a surface of said sample, and
   analyzing photoelectrons emitted by said sample surface in a time-of-flight electron detector.

16. An apparatus of a tunable, high resolution electron spectroscopy for chemical analysis (ESCA) system utilizing laser harmonics for investigating features on a sample with high spatial resolution comprising:
   a laser source for providing a pulsed laser beam for producing odd multiple harmonics in a noble gas,
   a reflective grating for selecting a beam of a predetermined laser harmonic and tuning a preset frequency,
   means for focussing the beam into a spot sufficiently small for investigating surface features of said sample,
   a positioner for positioning said sample under investigation, and
   an electron detection means for detecting the photoelectrons emitted from said sample surface.

17. An apparatus according to claim 16, wherein said laser source is a dye laser or a titanium-sapphire laser.

18. An apparatus according to claim 16, wherein said laser source is a pulsed laser.

19. An apparatus according to claim 16, wherein said reflective grating tunes the laser beam to said predetermined laser harmonic between the 3rd and the 39th harmonic.

20. An apparatus according to claim 16, wherein said focussing means focusses the beam to less than 1 micron in diameter.

21. An apparatus according to claim 16, wherein said electron detection means is a time-of-flight electron detector or an electrostatic analyzer.

* * * * *